United States Patent [19]

Kokotailo

[11] 4,289,607

[45] Sep. 15, 1981

[54] CATALYTIC CONVERSION WITH CRYSTALLINE ZEOLITE PRODUCT CONSTITUTING ZSM-5/ZSM-11 INTERMEDIATES

[75] Inventor: George T. Kokotailo, Woodbury, N.J.

[73] Assignee: Mobil Oil Corporation, New York, N.Y.

[21] Appl. No.: 156,702

[22] Filed: Jun. 5, 1980

Related U.S. Application Data

[63] Continuation-in-part of Ser. No. 28,482, Apr. 9, 1979, Pat. No. 4,229,424.

[51] Int. Cl.$^3$ .................... C10G 11/02; C10G 35/04; C07C 2/68
[52] U.S. Cl. .................................. 208/120; 208/134; 585/467; 585/469; 585/481; 585/533; 585/639
[58] Field of Search ............... 208/120, 134; 585/469, 585/639, 533, 467, 481

[56] References Cited

U.S. PATENT DOCUMENTS

| | | | |
|---|---|---|---|
| 3,702,886 | 11/1972 | Argauer et al. | 423/328 |
| 3,709,979 | 1/1973 | Chu | 423/329 |
| 3,941,871 | 3/1976 | Dwyer | 423/328 |
| 4,061,724 | 12/1977 | Grose et al. | 423/335 |

Primary Examiner—Curtis R. Davis
Attorney, Agent, or Firm—C. A. Huggett; R. W. Barclay; G. W. Allen

[57] ABSTRACT

A new crystalline aluminosilicate zeolite product is provided having a structure intermediate that of ZSM-5 and ZSM-11, having a characterizing X-ray diffraction pattern and having a unit cell parameter of at least about 40 Angstroms. There is also provided a method for synthesizing the new zeolite and a process for using the same as a catalyst in effecting conversion of organic compounds.

18 Claims, 5 Drawing Figures

FIG. 1 ZSM-5

FIG. 2  ZSM-11

CATALYTIC CONVERSION WITH CRYSTALLINE ZEOLITE PRODUCT CONSTITUTING ZSM-5/ZSM-11 INTERMEDIATES

CROSS REFERENCE TO RELATED APPLICATION

This application is a continuation-in-part of copending application Ser. No. 028,482 filed Apr. 9, 1979, now U.S. Pat. No. 4,229,424.

BACKGROUND OF THE INVENTION

1. Field of the Invention

This invention relates to novel crystalline porous tectosilicates, sometimes hereinafter referred to as porotektosilicates, constituting unobvious intermediates of two known zeolites to yield unique products, to methods for their preparation and to organic compound conversion, especially hydrocarbon conversion, therewith.

2. Discussion of the Prior Art

Zeolite materials, both natural and synthetic, have been demonstrated in the past to have catalytic capabilities for various types of organic compound conversion. Certain zeolitic materials are ordered porous crystalline aluminosilicates having a definite crystalline structure within which there a large number of cavities and channels, which are precisely uniform in size. Since the dimensions of these pores are such as to accept for adsorption molecules of certain dimensions while rejecting those of larger dimensions, these materials have been referred to as "molecular sieves" and are utilized in a variety of ways to take advantage of these properties.

Such molecular sieves include a wide variety of positive ion-containing crystalline aluminosilicates, both natural and synthetic. These aluminosilicates can be described as a rigid three-dimensional network of $SiO_4$ and $AlO_4$ in which the tetrahedra are cross-linked by the sharing of oxygen atoms whereby the ratio of the total aluminum and silicon atoms to oxygen is 1:2. The electrovalence of the tetrahedra-containing aluminum is balanced by the inclusion in the crystal of a cation, for example an alkali metal or an alkaline earth metal cation. This can be expressed by formula wherein the ratio of Al to the number of various cations, such as Ca/2, Sr/2, Na, K or Li is equal to unity. One type of cation may be exchanged either in entirety or partially by another type of cation utilizing ion exchange techniques in a conventional manner. By means of such cation exchange, it has been possible to vary the size of the pores in the given aluminosilicate by suitable selection of the particular cation. The spaces between the tetrahedra are occupied by molecules of water prior to dehydration.

Prior art techniques have resulted in the formation of a considerable number of synthetic crystalline aluminosilicates, among which are zeolite ZSM-5 described in U.S. Pat. No. 3,702,886, the entire contents of which are incorporated herein by reference and ZSM-11 described in U.S. Pat. No. 3,709,979, the entire contents of which are incorporated herein by reference. Both of the aforenoted zeolites, i.e., ZSM-5 and ZSM-11, are characterized by a unit cell parameter, hereinafter described in detail, of about 20 Angstrom units.

SUMMARY OF THE INVENTION

The present invention relates to a unique crystalline porous tectosilicate possessing a structure intermediate that of ZSM-5 and ZSM-11, hereinafter referred to as a ZSM-5/ZSM-11 intermediate having, in the sodium form, the characteristic X-ray diffraction pattern set forth in Table 1 hereinbelow and a unit cell parameter of at least about 40 Angstroms. The present invention also is directed to methods for preparation of the specified ZSM-5/ZSM-11 intermediates and to organic compound, e.g., hydrocarbon, conversion processes conducted therewith. The ZSM-5/ZSM-11 intermediate compositions can also be identified, in their anhydrous state, in terms of mole ratios of oxides as follows:

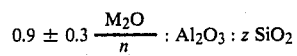

$$0.9 \pm 0.3 \frac{M_2O}{n} : Al_2O_3 : z\, SiO_2$$

where M is a cation, n is the valence of such cation, z is at least 5. In a preferred synthesized form, the ZSM-5/ZSM-11 intermediate has a formula in the anhydrous state, and in terms of mole ratios of oxides as follows:

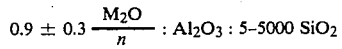

$$0.9 \pm 0.3 \frac{M_2O}{n} : Al_2O_3 : 5\text{--}5000\, SiO_2$$

where M has the above noted significance and preferably is hydrogen or a hydrogen precursor, e.g., ammonium cation.

The original cations can be replaced in accordance with techniques well-known in the art, at least in part, by ion exchange with other cations. Preferred replacing cations include metal ions, ammonium ions, hydrogen ions and mixtures of the same. Particularly preferred cations are those which render the zeolite intermediate composition catalytically active, especially for hydrocarbon conversion. These include hydrogen, rare earth metals, aluminum, manganese and metals of Groups II and VIII of the Periodic Table.

The ZSM-5/ZSM-11 intermediate compositions described herein possess a distinquishing crystalline structure whose X-ray diffraction pattern when M is sodium shows the following significant lines:

TABLE 1

| Interplanar Spacing d(A): | Relative Intensity |
|---|---|
| 11.2 ± 0.2 | v.s. |
| 10.1 ± 0.2 | v.s. |
| 6.73 ± 0.14 | W |
| 4.63 ± 0.08 | W |
| 3.86 ± 0.07 | S |
| 3.72 ± 0.07 | m-s |
| 2.01 ± 0.02 | W |

These values were determined by standard techniques. The radiation was the K-alpha doublet of copper, and a scintillation counter spectrometer with a strip chart pen recorder was used. The peak heights, I, and the positions as a function of 2 times theta, where theta is the Bragg angle were read from the spectrometer chart. From these, the relative intensities, 100 $I/I_o$ where $I_o$ is the intensity of the strongest line or peak and d(obs.), the interplanar spacing in Å, corresponding to the recorded lines, were calculated. In Table 1, the relative intensities are given in terms of the symbols s.=strong, w.=weak, m-s=medium strong and v.s.=very strong. In terms of intensities, these may be generally designated as:

v.s.=60-100
s.=40-60
m.=20-40
w.=0-20

It will be understood that that the above X-ray diffraction pattern is characteristic of all the species of the ZSM-5/ZSM-11 intermediate compositions. Ion exchange of the cations present in the as-synthesized form reveals substantially the same pattern with some minor shifts in interplanar spacing and variation in relative intensity. Other minor variations may occur depending on the silicon to aluminum ratio and thermal history of the particular composition subjected to X-ray diffraction analysis.

The two end members of the ZSM-5/ZSM-11 intermediates, i.e., ZSM-5 and ZSM-11, are those species wherein adjacent layers are structurally related by either a mirror plane or by an inversion.

The ZSM-5/ZSM-11 intermediates, on the other hand, constituting the subject matter of this invention, are those species wherein adjacent layers are structurally related by both a mirror plane and an inversion, two symmetry operations well understood in crystallography. This will be more readily apparent from a consideration of the topologic drawings referred to hereinbelow.

DESCRIPTION OF SPECIFIC EMBODIMENTS

Figure 1:
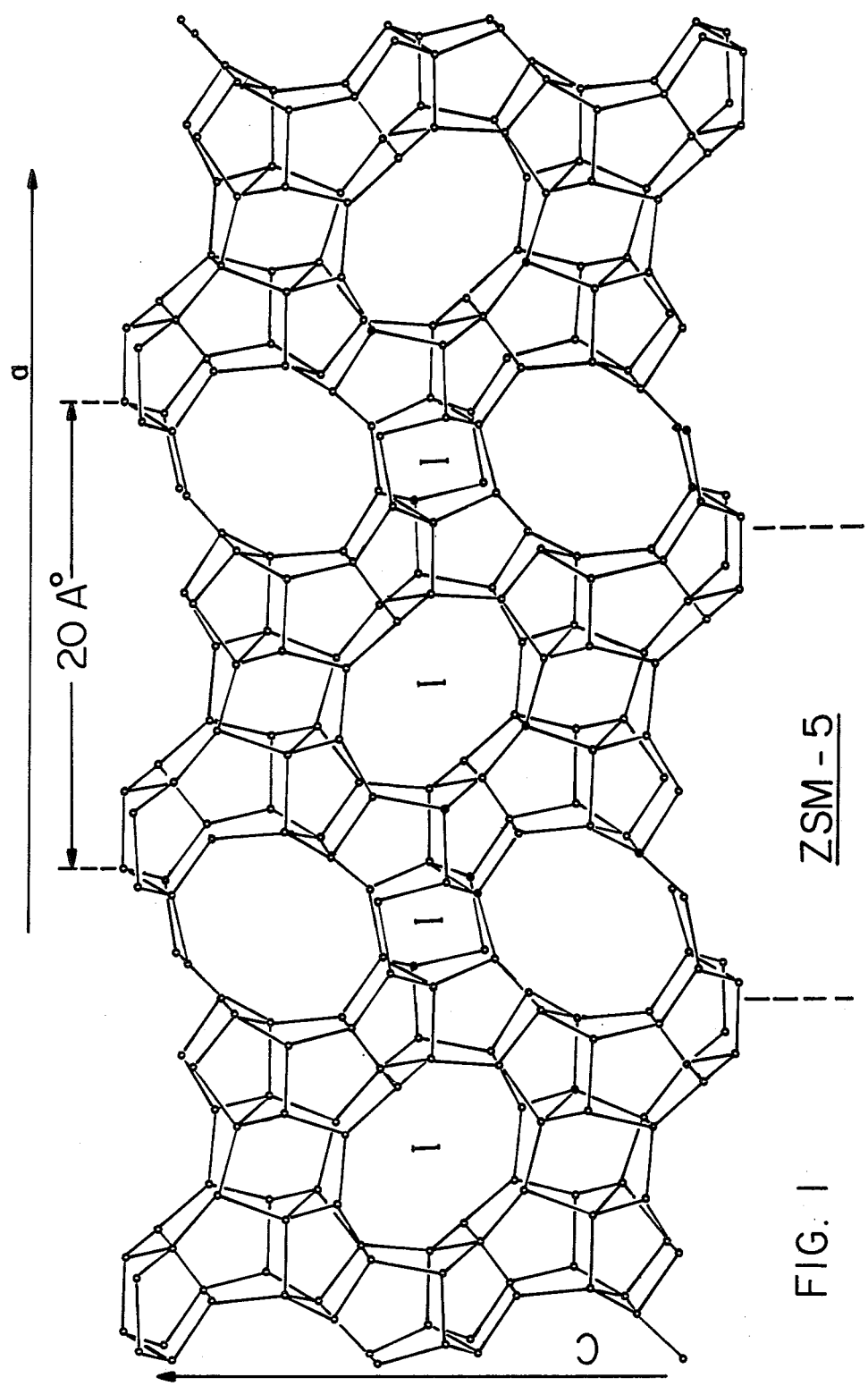
FIG. 1 is a topologic drawing depicting the structure of ZSM-5 made up of adjacent layers along the unit cell "a" axis structurally related by an inversion designated I. The unit cell dimension indicated by dashed vertical lines is about 20 Angstroms.
Figure 2:
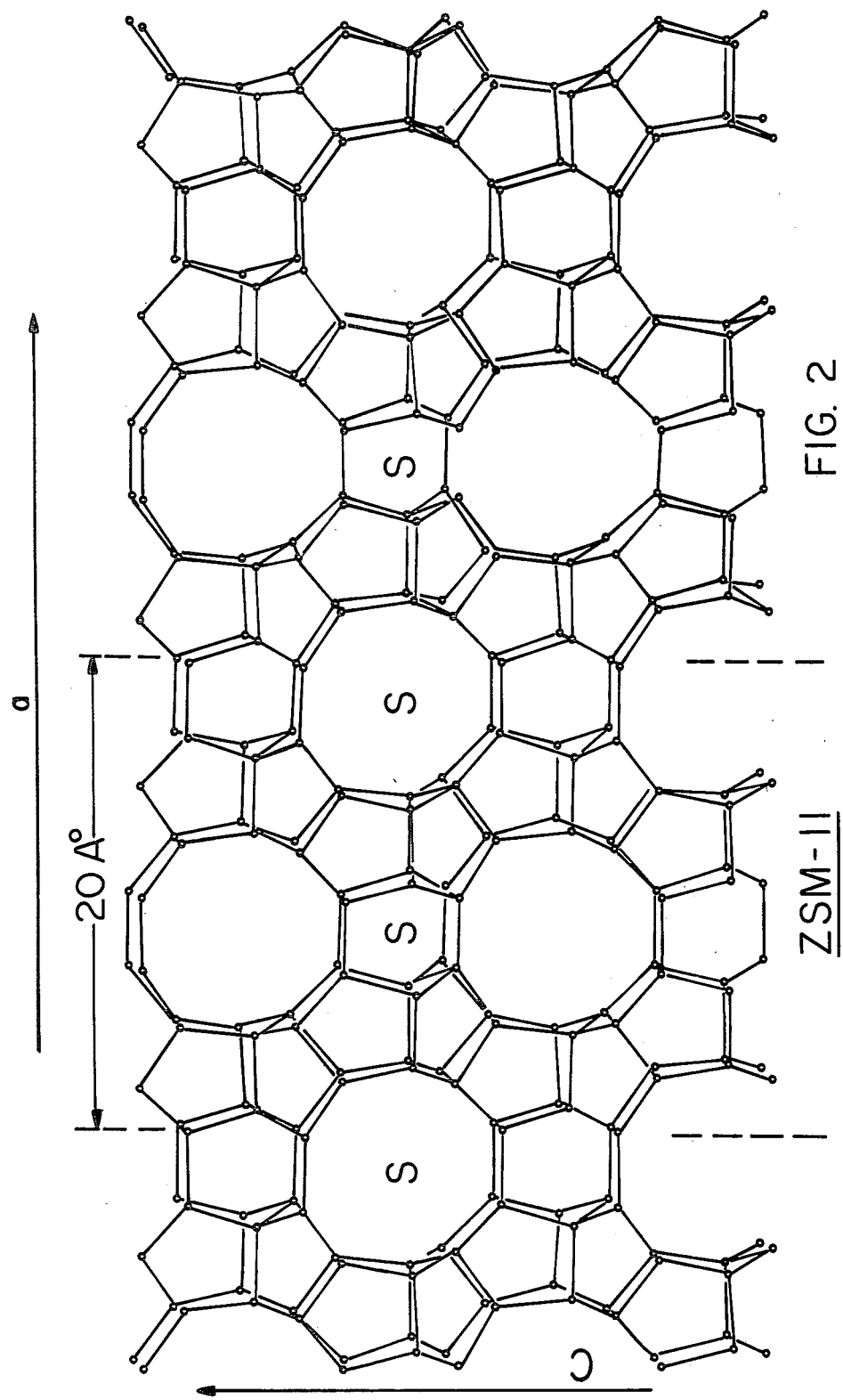
FIG. 2 is a topologic drawing depicting the structure of ZSM-11 made up of adjacent layers along the unit cell "a" axis structurally related by mirror planes depicted S. Again, the unit cell dimension indicated by dashed vertical lines is about 20 Angstroms.
Figure 3:
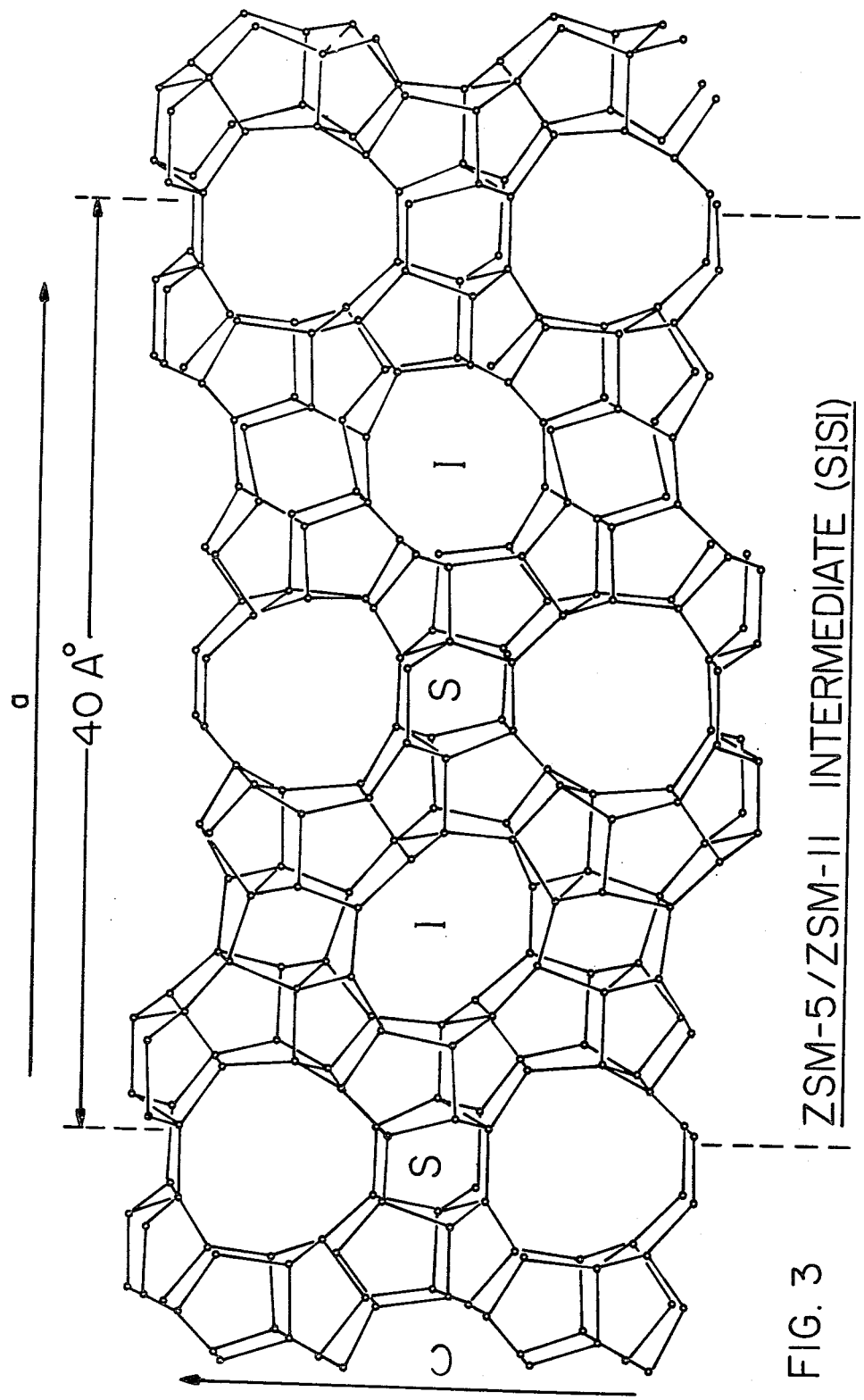
FIG. 3 is a topologic drawing depicting the structure of a ZSM-5/ZSM-11 intermediate made up of adjacent layers along the unit cell "a" axis structurally related by an inversion and mirror planes depicted SISI. The unit cell dimension indicated by dashed vertical lines, in this instance, is about 40 Angstroms.
Figure 4:
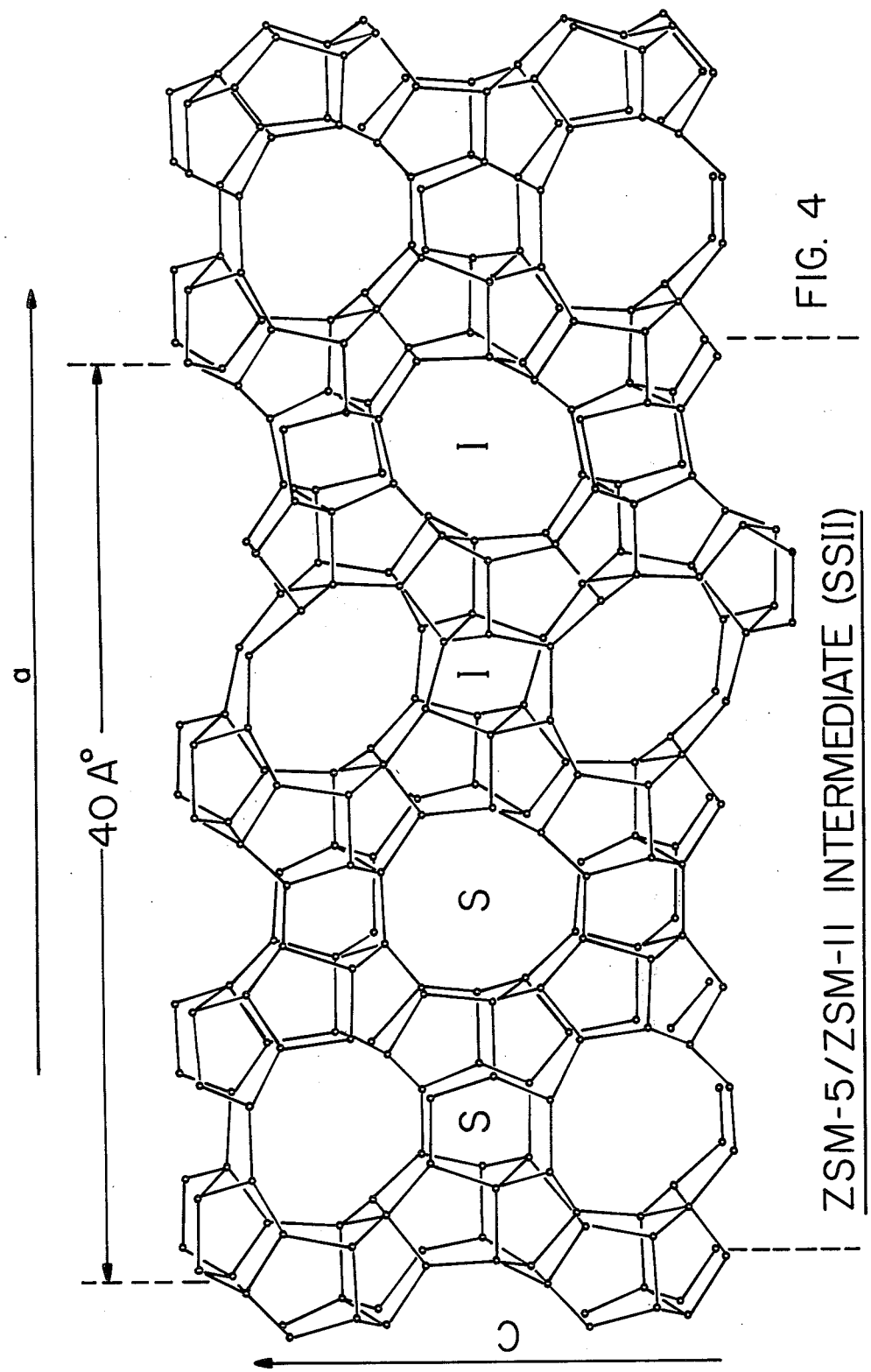
FIG. 4 is a topologic drawing again depicting the structure of a ZSM-5/ZSM-11 intermediate made up of adjacent layers along the unit cell "a" axis structurally related by an invesion and mirror planes designated SSII. The unit cell dimension, as indicated by the dashed vertical lines, is about 40 Angstroms.
Figure 5:
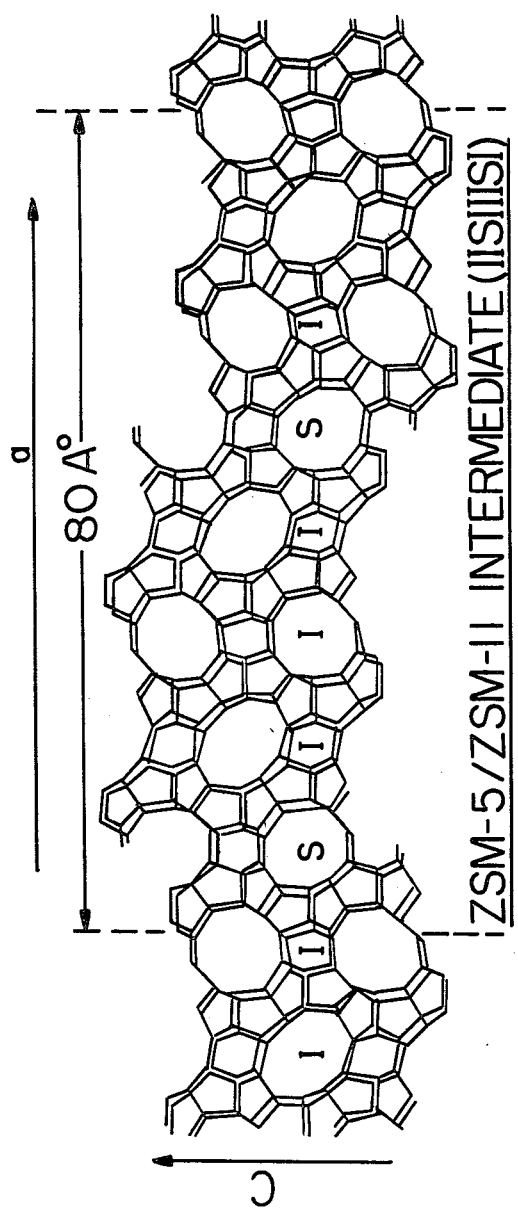
FIG. 5 is a topologic drawing showing still another ZSM-5/ZSM-11 intergrowth made up of adjacent layers along the unit cell "a" axis structurally related by an inversion and mirror planes depicted IISIIISI. The unit cell dimension, in this instance, is about 80 Angstroms.

The compositions of this invention constitute crystalline porous tectosilicate zeolites characterized by a structure intermediate that of ZSM-5 and ZSM-11 having, in the sodium form, an X-ray powder diffraction pattern set forth in Table 1 hereinabove and having a unit cell parameter of at least about 40 Angstroms.

The unit cell dimension of the compositions described herein approximates at least 40 Angstroms and may exceed such minimum by additional multiples of at least 20 Angstroms. That is, the unit cell dimension may be 40+20 (n) Å where n is an integral number.

Unit cell dimension, as such expression is utilized herein, is used in the conventional sense, as understood by those skilled in the art and may be determined by electron or X-ray diffraction analyses, as described, for example, in "X-ray Diffraction Procedures" by H. P. Klug and L. E. Alexander, John Wiley & Sons, 1954 and in "Interpretation of Electron Diffraction Patterns" by K. W. Andrews, D. J. Dyson and S. R. Keown, Plenum Press 1967. As described in these references, sufficiently small single crystals so as to afford penetration of the electron beam are aligned to yield reflections. The analysis of these electron diffraction patterns of single crystals will give the lattice parameters a, b and c. If the crystal structure is not periodic but contains a number of random stacking faults then the electron diffraction spots will be streaked.

In addition to the ordered ZSM-5/ZSM-11 intermediates described hereinabove, other combinations, such as, for example, SSSISI and IISISI are possible. Both of these structures would have a unit cell dimension of about 60 Angstroms. Table 2 set forth below lists some of the possible ordered ZSM-5/ZSM-11 intermediate structures. Random intermediates of ZSM-5/ZSM-11 are also possible.

TABLE 2

| Symmetry Progression | Unit Cell Dimension (Å) |
|---|---|
| SS (ZSM-11) | 20 |
| II (ZSM-5) | 20 |
| SS II | 40 |
| SI SI | 40 |
| SS SSII | 60 |
| II SSII | 60 |
| SS SISI | 60 |
| II SISI | 60 |
| SS SSSSII | 80 |
| II SSSSII | 80 |
| II IISSII | 80 |
| SS SSSISI | 80 |
| II SSSISI | 80 |
| SS IISISI | 80 |
| II IISISI | 80 |
| SSSISSSI | 80 |
| IISIIISI | 80 |
| SSSIIISI | 80 |

The above-described ZSM-5/ZSM-11 intermediate compositions, when employed either as adsorbent or as catalysts should be dehydrated at least partially. This can be done by heating to a temperature in the range of 200° to 600° C. in an atmosphere such as air, nitrogen or other inert gas and at atmospheric or subatmospheric pressure for between 1 and 48 hours. Dehydration can also be performed at lower temperatures by merely placing the intergrowth zeolite in a vacuum but a longer time is required to obtain a sufficient amount of dehydration.

The ZSM-5/ZSM-11 intermediate zeolite compositions of this invention may be prepared by forming a solution containing a quarternary compound of an element of Group 5A of the Periodic Table, sodium oxide, water and having a composition, in terms of mole ratios of oxides, falling within the following ranges:

TABLE 2

| | Broad | Preferred |
|---|---|---|
| $Na_2O/SiO_2$ | .001–.8 | .004–.5 |
| $(R_4X)_2O/SiO_2$ | .01–.5 | .02–.3 |
| $H_2O/Na_2O$ | 20–1000 | 100–700 |

| TABLE 2-continued | | |
|---|---|---|
| | Broad | Preferred |
| $SiO_2/Al_2O_3$ | 5–5000 | 150–3000 | where $R_4X^+$ is a cation of a quarternary compound of an element of Group 5A of the Periodic Table and maintaining the mixture until crystals of the zeolite are formed. Thereafter, the crystals are separated from the liquid and recovered. Typical reaction conditions consist of heating the foregoing reaction mixture to a temperature of from about 100° C. to 175° C. for a period of time of from about 6 hours to 60 days. A more preferred temperature range is from about 150° to 175° C. with the amount of time at a temperature in such range being from about 12 hours to 24 days. The separated solid product, after water washing, is dried for example, at 230° F. for at least 3 hours, e.g., 8 to 24 hours.

It will be understood that the described zeolite compositions can be prepared utilizing materials which supply the appropriate oxide. Such compositions include sodium aluminate, alumina, sodium silicate, silica hydrosol, silica gel, silicic acid and sodium hydroxide. The quarternary compounds can be any element of Group 5A, such as nitrogen, phosphorus, arsenic, antimony or bismuth. The compound is generally expressed as $R_4X^+$ wherein X is an element of Group 5A of the Periodic Table and each R is an alkyl or aryl group having between 1 and 7 carbon atoms. While normally each alkyl or aryl group will be the same, it is not necessary that each group have the same number of carbon atoms in the chain. The oxide of the quarternary compound is generally supplied by introducing into the reaction mixture a composition such as tetramethyl, tetraethyl, tetrapropyl or tetrabutyl hydroxide or halide of the Group 5A elements. In preparing an ammonium species, tetrabutyl ammonium chloride or hydroxide is especially useful. In preparing the phosphonium species of the zeolite, tetrabutylphosphonium chloride is particularly desirable as a means of incorporating the quarternary compound in the zeolite. The other elements of Group 5A behave similarly and thus zeolites containing the same can be prepared by the same manipulative procedure substituting the other Group 5A metals for phosphorus.

It will be understood that each oxide component utilized in the reaction mixture can be supplied by one or more initial reactants and they can be mixed together in any order. Thus, sodium oxide can be supplied by an aqueous solution of sodium hydroxide or by an aqueous solution of sodium silicate. The reaction mixture can be prepared either batchwise or continuously. Crystal size and crystallization time of the resulting zeolite composition will vary with the nature of the reaction mixture employed.

The ZSM-5/ZSM-11 intermediate compositions described herein may be used for organic compound conversion in the hydrogen form or they may be base exchanged or impregnated to contain ammonium or a metal cation complement. It is desirable to calcine the catalyst after base exchange. The metal cations that may be present include any of the cations of the metals of Groups I through VIII of the Periodic Table, especially rare earth metals. However, in the case of Group IA metals, the cation content should in no case be so large as to effectively inactivate the catalyst.

As in the case of many catalysts, it may be desirable to incorporate the catalyst composition described herein with another material resistant to the temperature and other conditions employed in some organic compound conversion processes. Such matrix materials include active and inactive materials and synthetic or naturally occurring zeolites as well as inorganic material such as clays, silica and/or metal oxides. The latter may be either naturally occurring or in the form of gelatinous precipitates, sols or gels including mixtures of silica and metal oxides. Inactive materials suitably serve as diluents to control the amount of conversion in a given process so that products can be obtained economically and orderly without employing other means for controlling the rate of reaction. Frequently, zeolite materials have been incorporated into naturally occurring clays, e.g., bentonite and kaolin. These materials, i.e., clays, oxides, etc., function, in part, as binders for the catalyst. It may be desirable to provide a catalyst having good crush strength so it may be used in a process where the catalyst is subjected to rough handling, such as in a moving bed system, which may tend to break the catalyst down into powder-like materials which cause problems in processing.

Naturally occurring clays which can be composited with the improved zeolites prepared hereby include the montmorillonite and kaolin families, which include the sub-bentonites and the kaolins commonly known as Dixie, McNammee, Georgia and Florida clays or others in which the main mineral constituent is halloysite, kaolinite, dickite, nacrite and anauxite. Such clays can be used in the raw state, as originally mined, or initially subjected to calcination, acid treatment or chemical modification.

In addition to the foregoing materials, the zeolites made hereby can be composited with one or more porous matrix materials such as alumina, silica-alumina, silica-magnesia, silica-zirconia, silica-thoria, silica-beryllia, silica-titania, titania-zirconia as well as ternary compositions such as silica-alumina-thoria, silica-alumina-zirconia, silica-alumina-magnesia and silica-magnesia-zirconia. The matrix can be in the form of a cogel. A mixture of these components, one with the other and/or with a clay, could also be used. The relative proportions of zeolite and inorganic oxide gel matrix and/or clay vary widely with the crystalline aluminosilicate content ranging from about 1 to about 90 percent by weight and more usually in the range of about 2 to about 50 percent by weight of the composite.

The ZSM-5/ZSM-11 intermediate crystalline porous tectosilicates described herein are valuable catalysts in various organic compound, conversion processes, e.g., the conversion of hydrocarbon compounds and oxygenates such as methanol. These processes include, for example, alkylation of aromatics with olefins, aromatization of normally gaseous olefins and paraffins, aromatization of normally liquid low molecular weight paraffins and olefins, isomerization of aromatics, paraffins and olefins, disproportionation of aromatics, transalkylation of aromatics, oligomerization of olefins and cracking and hydrocracking. All of the foregoing catalytic processes are of value since they result in upgrading of the organic charge being processed.

The process for upgrading reformates utilizing the ZSM-5/ZSM-11 intermediate composition described herein as catalyst generally involves contact during processing with a reformate or reformer effluent, with or without added hydrogen, at a temperature between 500° F. and about 1100° F. and preferably between about 550° F. and about 1000° F. The reaction pressure in such operation is generally within the range of about 25 and about 2000 psig and preferably about 50 to about 1000 psig. The liquid hourly space velocity, i.e., the liquid volume of hydrocarbon per hour per volume of catalyst, is between about 0.1 and about 250, and preferably between about 1 and 100. Although hydrogen is not essential to this process, when it is used the molar ratio of hydrogen to hydrocarbon charge employed is between about 0.1 and about 80 preferably between about 1 and about 10.

Oligomerization of olefins, i.e., olefins having 2 to 10 carbon atoms, is effectively carried out with the described zeolite composition as catalyst. Such reaction is suitably effected at a temperature between about 550° F. and about 1150° F., a pressure between about 0.01 and about 1000 psig utilizing a weight hourly space velocity within the approximate range of 0.1 to 1000.

Alkylation of aromatic hydrocarbons, e.g., benzene, with an alkylating agent such as an alkyl halide, an alcohol or an olefin, is also readily effected in the presence of the ZSM-5/ZSM-11 intermediate as catalyst with reduced aging. Alkylation conditions include a temperature between about 400° F. and about 1000° F., a pressure between about 25 and about 1000 psig utilizing an aromatic hydrocarbon/alkylating agent mole ratio of 2 to 200 and an alkylating agent weight hourly space velocity within the approximate range of 0.5 to 50.

Xylene isomerization is another reaction suitably conducted in the presence of the described ZSM-5/ZSM-11 intermediate as catalyst. Isomerization conditions include a temperature between about 300° F. and about 900° F., a pressure between about 25 and about 1000 psig, utilizing a weight hourly space velocity within the approximate range of 0.2 to 100.

Aromatics, such as, for example, toluene, may be disproportionated in the presence of the ZSM-5/ZSM-11 intermediate zeolite at a temperature of from about 450° F. to about 1100° F., a pressure of from about 50 psig to about 800 psig and a liquid hourly space velocity within the approximate range of about 0.1 to about 20. Aliphatic hydrocarbons may also be disproportionated in the presence of the described ZSM-5/ZSM-11 intermediate zeolites, at a temperature of from about 350° F. to about 900° F., a pressure between 0 and 3,000 psig and a liquid hourly space velocity of between about 0.01 and about 5.

When the conversion of organic compounds with the ZSM-5/ZSM-11 intermediate zeolite as catalyst involves cracking, catalytic conversion conditions should be maintained within certain ranges, including a temperature of from about 700° F. to about 1200° F., preferably from about 800° F. to about 1000° F., a pressure of from about atmospheric to about 200 psig, and a liquid hourly space velocity of from about 0.5 $hr^{-1}$ to about 50 $hr^{-1}$, preferably from about 1 $hr^{-1}$ to about 10 $hr^{-1}$. Cracking activity of the ZSM-5/ZSM-11 intermediate zeolite is conveniently measured by the alpha-test for determining the relative cracking activity in the cracking of hexane for the catalyst under test with a silica-alumina amorphous cracking catalyst (90% $SiO_2$—10% $Al_2O_3$) having an alpha value of one. This test method and a fuller development of the activity is described in an article by P. B. Weisz and J. N. Miale appearing in the Journal of Catalysis, Vol. 4, No. 4 (August 1965) at pages 525–529, contents of which are incorporated herein by reference. When the conversion is hydrocracking, catalytic conversion conditions should be maintained within somewhat different ranges, including a temperature of from about 400° F. to about 1000° F., preferably from about 500° F. to about 850° F., a pressure of from about 500 psig to about 3500 psig, a liquid hourly space velocity of from about 0.1 $hr^{-1}$ to about 10 $hr^{-1}$, preferably from about 0.2 $hr^{-1}$ to about 5 $hr^{-1}$, and a hydrogen/hydrocarbon ratio of from about 1000 scf/bbl to about 20,000 scf/bbl, preferably from about 3,000 scf/bbl to about 10,000 scf/bbl.

It may be desirable in some instances to add a hydrogenation/dehydrogenation component to the ZSM-5/ZSM-11 intermediate for use as catalyst. The amount of the hydrogenation/dehydrogenation component employed is not narrowly critical and can range from about 0.01 to about 30 weight percent based on the entire catalyst. A variety of hydrogenation components may be combined with either the zeolite and/or matrix in any feasible manner which affords intimate contact of the components, employing well known techniques such as base exchange, impregnation, coprecipitation, cogellation, mechanical admixture of one component with the other and the like. The hydrogenation component can include metals, oxides and sulfides of metals of the Periodic Table which fall in Group VI-B including chromium, molybdenum and tungsten; Group II-B including zinc and cadmium; Group VIII including cobalt, nickel, platinum, palladium, ruthenium, rhodium, osmium and iridium; Group IV-A such as germanium and tin and combinations of metals, sulfides and oxides of metals of Group VI-B and VIII, such as nickel-tungsten-sulfide, cobalt oxide-molybdenum oxide and the like. Pre-treatment before use varies depending on the hydrogenation component present. For example, with components such as nickel-tungsten, cobalt-molybdenum, platinum and palladium, the catalyst may desirably be sulfided. With metals like platinum and palladium, a hydrogenation step may also be employed. These techniques are well known in the art and are accomplished in a conventional manner.

In order to more fully illustrate the nature of the invention and the manner of practicing same, the following examples are presented.

EXAMPLE 1

A silicate solution was prepared by mixing 3440 g of sodium silicate (27.8% $SiO_2$; 8.42% $Na_2O$ and 63.7% $H_2O$), 20 g of sodium salt of a polymerized substituted benzenoid alkyl sulfonic acid combined with an inert organic suspending agent (Daxad 27) and 4000 g of $H_2O$. An acid solution was made by mixing together 425 g of tetrapropylammonium bromide, 88 g of 50% wt solution of tetramethylammonium chloride, 345 g of $H_2SO_4$ and 4000 g of water. The specific gravity of the above two solutions were 1.152 and 1.049 at 60° F., respectively.

The solutions were charged simultaneously into a stirred 5 gallon capacity autoclave to form a homogeneous gel. The pH of the gel was measured to be 9.6. The crystallization was carried out at 320° F. with 90 rpm agitation for 12 hours. The washed and dried product was found to be a crystalline aluminosilicate characterized by an X-ray diffraction pattern as shown in Table 1. The composition of the product was analyzed and was found to be as follows:

| | |
|---|---|
| $SiO_2$ | 82.9% wt. |

| | |
|---|---|
| Al$_2$O$_3$ | 0.28% wt. |
| Na | 0.70% wt. |
| N | 0.81% wt. |
| C | 9.11% wt. |
| Ash | 86.8% wt. |

EXAMPLE 2

A clear solution was prepared by mixing 45 g of sodium silicate (27.8% SiO$_2$; 8.42% Na$_2$O and 63.78% H$_2$O) and 5.5 g of tetrabutylphosphonium chloride in 150 g of water. Another solution was made by dissolving 0.5 g of AlCl$_3$.6H$_2$O, 1 g of SnCl$_4$.5H$_2$O, 9 g of HCl (37%) in 150 g of H$_2$O. Both solutions were filtered to get rid of any particulate impurities. Solutions were poured into a pressure bomb to form gel. The crystallization was carried out at 330° F. for 17 days. The product was filtered, water-washed and oven-dried. X-ray diffraction identified the product as having the pattern shown in Table 1.

EXAMPLE 3

A solution was made by dissolving 1.5 g of NaAlO$_2$, 6.5 g of NaOH and 20 g of tetrabutylammonium bromide into 300 g of water. To the solution, 75 g of precipitated silica (Hi-Sil) was added. The crystallization was carried out at 325° F., without agitation for 3 days. The water-washed and dried product was found to be a crystalline aluminosilicate characterized by an X-ray diffraction pattern as shown in Table 1.

EXAMPLE 4

Twenty (20) g of tetrabutylammonium bromide, 20 g of Na$_3$PO$_4$.12H$_2$O and 1.5 g of NaAlO$_2$ were dissolved in 300 g of distilled water. Seventy-five grams of precipitated silica (Hi-Sil) were added to the solution to form a uniform slurry. The crystallization was at 300° F. for 4 days. The product was found to be a crystalline aluminosilicate characterized by an X-ray diffraction pattern as shown in Table 1. The chemical composition of the water-washed and dried sample was analyzed to be

| | |
|---|---|
| SiO$_2$ | 87.9% wt. |
| Al$_2$O$_3$ | 1.24% wt. |
| Na | 0.56% wt. |
| N | 0.53% wt. |
| C | 8.83% wt. |
| P | 0.21% wt. |
| Ash | 87.7% wt. |

EXAMPLE 5

A solution was made by dissolving 1.5 g. of NaAlO$_2$, 20 g of tetrabutylammonium bromide and 10 g of Na$_2$CO$_3$ in 300 g of H$_2$O. Seventy-five grams of precipitated silica (Hi-Sil) were then added to the solution to form a homogeneous slurry. The crystallization was carried out at 300° F. for 5 days. The water-washed and dried crystalline product had an X-ray diffraction pattern as shown in Table 1.

EXAMPLE 6

A silicate solution was made by mixing 45 g of sodium silicate 27.8% SiO$_2$,8.42% Na$_2$O and 63.78% H$_2$O), 11 g of tetrabutylphosphonium chloride and 150 g of water. An acid alum solution was made by mixing 0.5 g of Al$_2$(SO$_4$)$_3$.14H$_2$O, 10 g of 50% tetramethylammonium chloride solution, 4.2 g of H$_2$SO$_4$ and 150 g of distilled water. Both solutions were filtered to remove particulate impurities. Forty-four ml of the acid alum solution was mixed with 50 ml of silicate solution to form a gel. The pH of the gel was measured to be 9.2. The crystallization of the gel was carried out at 330° F. for 10 days. The X-ray diffraction analysis showed the product to have the pattern set forth in Table 1.

EXAMPLE 7

A dilute silicate solution was made by mixing 50 g of sodium silicate (27.8% SiO$_2$, 8.42% Na$_2$O and 63.78% H$_2$O), 100 g of triethanaolamine and 300 g of H$_2$O. An acidic solution was made by dissolving 25 g of tetrabutylphosphonium chloride, 4.8 g of H$_2$SO$_4$ and 100 g of triethanolamine in 300 g of H$_2$O. 100 ml each of the above two solutions were mixed to provide a uniform gel. The gel pH was measured to be 10.5. The crystallization of the gel was carried out at 212° F. for 35 days. The waterwashed and dried product was crystalline and determined to have the X-ray powder diffraction pattern of Table 1.

EXAMPLE 8

A solution was made by dissolving 1.5 grams of Na AlO$_2$, 10.5 grams of NaOH, 10 grams of tetrabutylammonium bromide and 10 grams of tetramethylammonium bromide in 300 grams of water. To the solution, 75 grams of precipitated silica (Hi-Sil) was added and the resulting mixture stirred in a blender for 15 minutes. Crystallization was carried out at 330° F., without agitation, for 28 days. The water-washed and dried product was found to be a crystalline aluminosilicate characterized by an X-ray diffraction pattern as shown in Table 1.

EXAMPLE 9

A solution was prepared by dissolving 1.5 grams of NaAlO$_2$, 6.5 grams of NaOH and 10 grams of tetrabutylammonium bromide in 300 grams of water. To the solution was added 50 grams of pyrrolidine and thereafter 75 grams of precipitated silica (Hi-Sil). The resulting mixture was stirred in a blender for 15 minutes. Crystallization was carried out at 340° F., without agitation, for 19 days. The water-washed and dried product was found to be a crystalline aluminosilicate characterized by an X-ray diffraction pattern as shown in Table 1.

EXAMPLE 10

A solution was made by dissolving 1.5 grams of NaAlO$_2$, 9 grams of NaOH, 10 grams of tetrabutylammonium bromide and 10 grams of tetramethylammonium bromide in 300 grams of water. To the solution, 75 grams of precipitated silica (Hi-Sil) was added and the resulting mixture stirred in a blender for 15 minutes. Crystallization was carried out at 360° F., without agitation, for 15 days. The water-washed and dried product was found to be a crystalline aluminosilicate characterized by an X-ray diffraction pattern as shown in Table 1.

EXAMPLE 11

A solution was prepared by dissolving 2.1 grams of Al(NO$_3$)$_3$.9H$_2$O, 6.9 grams of NaOH, 22 grams of tetraethylammonium bromide in 340 grams of water. To the solution was added 50 grams of pyrollidine and thereafter 72 grams of precipitated silica (Hi-Sil). The resulting mixture was stirred in a blender for 15 minutes. Crystallization was carried out at 325° F., without agitation, for 14 days. The water-washed and dried product was found to be a crystalline aluminosilicate characterized by an X-ray diffraction pattern as shown in Table 1.

The aluminosilicate products of Examples 1, 3, 4, 5, 8, 9, 10 and 11 were converted to the hydrogen form and evaluated for catalytic cracking activity in the hereinabove referred to alpha cracking test.

For conversion to the hydrogen form, the products of Examples 1, 3, 4 and 5 were calcined 15 hours at 500° C. in a muffle furnace, then exchanged for 2 hours at 100° C. with 1 N NH4Cl solution, washed, filtered and the above exchange repeated. The ammonium form so obtained was calcined for 6 hours at 500° C. to yield the hydrogen form. The products of Examples 8, 9, 10 and 11 were calcined 10 hours at 500° C. in a muffle furnace, then exchanged twice for 2 hours each at 100° C. with 1n NH4Cl solution, washed and filtered. The ammonium form so obtained was calcined for 4 hours at 500° C. to yield the hydrogen form.

Cracking evaluation utilizing the alpha test gave the following results:

| Hydrogen Form of Product of Example | Alpha Activity |
|---|---|
| 1 | 7.5 |
| 3 | 127 |
| 4 | 111 |
| 5 | 151 |
| 8 | 155 |
| 9 | 188 |
| 10 | 140 |
| 11 | 90 |

Methanol conversion was carried out by contacting methanol with the hydrogen form of products of Examples 3 and 9 at a temperature of 700° F., a pressure of 1 atmosphere utilizing a liquid hourly space velocity of 1 to achieve 100 percent conversion of the methanol.

The hydrocarbon distribution obtained, in each instance, as a result of such conversion is shown below:

| Hydrogen Form of Product of Example | 9 | 3 |
|---|---|---|
| Hydrocarbon Distribution | | |
| $C_1$ | .70 | .91 |
| $C_2$ | .61 | |
| $C_2=$ | 1.10 | 1.94 |
| $C_3$ | 15.02 | 12.23 |
| $C_3=$ | 1.74 | 2.16 |
| $iC_4$ | 17.72 | 14.80 |
| $NC_4$ | 5.49 | 4.66 |
| $C_4=$ | 1.20 | 1.94 |
| $iC_5$ | 6.77 | 5.50 |
| $nC_5$ | 1.15 | 1.02 |
| $C_5=$ | .31 | .41 |
| $C_6$+Non-Aromatic | 4.29 | 7.14 |
| $C_6$ Aromatic | 1.25 | .90 |
| $C_7$ Aromatic | 11.14 | 11.40 |
| $C_8$ Aromatic | 19.16 | 21.77 |
| $C_9$ Aromatic | 8.73 | 9.96 |
| $C_{10}$ Aromatic(Durene) | 2.33 (.24) | 2.00 (.19) |
| $C_{11}$ Aromatic | 1.29 | 1.26 |
| $C_5$ Gasoline | 56.42 | 61.36 |
| Aromatics | 43.90 | 47.29 |

From the above tabulated data, it will be seen that the ZSM-5/ZSM-11 intermediate zeolite described herein was highly effective in conversion of methanol to gasoline of low durene content.

What is claimed is:

1. A process for conversion of an organic charge which comprises contacting the same under conversion conditions with a catalyst comprising a crystalline porous tectosilicate characterized by a structure intermediate that of ZSM-5 and ZSM-11 having in its sodium form, an X-ray diffraction pattern substantially as shown in Table 1 and having a unit cell parameter of at least about 40 Angstroms.

2. The process of claim 1 wherein said charge comprises an oxygenate.

3. The process of claim 2 wherein said oxygenate is methanol.

4. The process of claim 1 wherein said charge comprises a hydrocarbon.

5. The process of claim 1 wherein reformates are upgraded.

6. The process of claim 4 wherein hydrocarbon conversion involves oligomerization of olefins.

7. The process of claim 1 wherein said conversion involves alkylation of aromatic hydrocarbon.

8. The process of claim 4 wherein hydrocarbon conversion involves xylene isomerization.

9. The process of claim 4 wherein conversion involves cracking of a hydrocarbon charge.

10. The process of claim 1 wherein said crystalline porous tectosilicate is further characterized in its anhydrous state, by the formula:

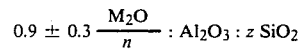
$$0.9 \pm 0.3 \frac{M_2O}{n} : Al_2O_3 : z\, SiO_2$$

where M is a cation, n is the valence of said cation and z is at least 5.

11. The process of claim 1 wherein said crystalline porous tectosilicate is further characterized by the formula:

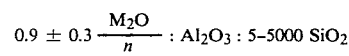
$$0.9 \pm 0.3 \frac{M_2O}{n} : Al_2O_3 : 5\text{--}5000\, SiO_2$$

where M is a cation and n is the valence of said cation.

12. The process of claim 10 where M is predominantly hydrogen.

13. The process of claim 11 where M is hydrogen.

14. The process of claim 1 wherein said crystalline porous tectosilicate is further characterized by having adjacent layers sructurally related by both a mirror plane and an inversion.

15. The process of claim 1 wherein said crystalline porous tectosilicate has the configuration SISI where S is a mirror plane and I is an inversion.

16. The process of claim 1 wherein said crystalline porous tectosilicate has the configuration ISSI where S is a mirror plane and I is an inversion.

17. The process of claim 1 wherein said crystalline porous tectosilicate has the configuration IISIIISI where S is a mirror plane and I is an inversion.

18. The process of claim 1 wherein said crystalline porous tectosilicate is combined with a matrix material.

* * * * *

UNITED STATES PATENT AND TRADEMARK OFFICE
CERTIFICATE OF CORRECTION

PATENT NO. : 4,289,607

DATED : September 15, 1981

INVENTOR(S) : George T. Kokotailo

It is certified that error appears in the above-identified patent and that said Letters Patent are hereby corrected as shown below:

Col. 2, line 49      After "11.2" insert --$\pm$--
Col. 3, line 50      "invesion" should read --inversion-- (both copies)
Col. 8, line 54      "4000 g" should read --4400 g--
Col. 12, line 50     "sructurally" should read --structurally--

Signed and Sealed this

Eighth Day of December 1981

[SEAL]

Attest:

Attesting Officer

GERALD J. MOSSINGHOFF

*Commissioner of Patents and Trademarks*